United States Patent
Johnson et al.

(10) Patent No.: US 11,324,856 B2
(45) Date of Patent: May 10, 2022

(54) BONE PUTTY FOR BONE PORE AND VOID FILLING

(71) Applicant: ZAVATION MEDICAL PRODUCTS LLC, Flowood, MS (US)

(72) Inventors: Jeffrey Johnson, Flowood, MS (US); Nels Lauritzen, Somerville, NJ (US); Brent Mitchell, Haskell, NJ (US)

(73) Assignee: ZAVATION MEDICAL PRODUCTS LLC, Flowood, MS (US)

( * ) Notice: Subject to any disclaimer, the term of this patent is extended or adjusted under 35 U.S.C. 154(b) by 298 days.

(21) Appl. No.: 16/296,465

(22) Filed: Mar. 8, 2019

(65) Prior Publication Data

US 2020/0282111 A1    Sep. 10, 2020

(51) Int. Cl.
| | |
|---|---|
| *A61L 27/38* | (2006.01) |
| *A61L 27/12* | (2006.01) |
| *A61L 27/58* | (2006.01) |
| *A61L 27/56* | (2006.01) |
| *A61L 27/26* | (2006.01) |
| *C08L 67/02* | (2006.01) |
| *A61L 24/00* | (2006.01) |
| *A61L 27/10* | (2006.01) |
| *A61L 27/36* | (2006.01) |
| *C07K 14/78* | (2006.01) |
| *A61L 27/46* | (2006.01) |

(52) U.S. Cl.
CPC ......... *A61L 27/3821* (2013.01); *A61L 27/12* (2013.01); *A61L 27/26* (2013.01); *A61L 27/56* (2013.01); *A61L 27/58* (2013.01); *A61L 24/0084* (2013.01); *A61L 27/10* (2013.01); *A61L 27/3608* (2013.01); *A61L 27/46* (2013.01); *A61L 2300/414* (2013.01); *C07K 14/78* (2013.01); *C08L 67/02* (2013.01)

(58) Field of Classification Search
None
See application file for complete search history.

(56) References Cited

U.S. PATENT DOCUMENTS

| | | | | |
|---|---|---|---|---|
| 2007/0066525 | A1* | 3/2007 | Lee | A61K 38/1875 514/200 |
| 2008/0187571 | A1* | 8/2008 | Clineff | A61L 27/46 424/426 |
| 2012/0195982 | A1* | 8/2012 | Hu | A61K 38/39 424/696 |
| 2012/0276164 | A1* | 11/2012 | Tuominen | A61K 6/891 424/400 |
| 2016/0136325 | A1* | 5/2016 | Brunelle | A61L 27/54 424/426 |

* cited by examiner

*Primary Examiner* — Robert A Wax
*Assistant Examiner* — Randeep Singh
(74) *Attorney, Agent, or Firm* — IP & T Group LLP

(57) ABSTRACT

A bone pore or void filling composition is described. The composition includes a mixture of: a type I collagen and/or a type I collagen-glycosaminoglycan coprecipitate; a blend of polyethylene glycol polymers having different molecular weights; a bone growth stimulator; and bioactive glass. A kit for containing the bone pore or void filling composition, and methods for using the composition to fill a bone pore or void are also described.

15 Claims, 5 Drawing Sheets

BONE PUTTY FOR BONE PORE AND VOID FILLING

BACKGROUND

Bone putty is used to correct surgical defects that may be caused by trauma, pathological disease, surgical intervention or other situations where defects need to be managed in osseous surgery. It is important to have the defect filler in the form of a stable, viscous putty to facilitate the placement of the bone growth medium into the surgical site which is usually uneven in shape and depth. The surgeon will take the putty on a spatula or other instrument and trowel it into the site, or take it in his/her fingers to shape the bone inducing material into the proper configuration to fit the site being corrected.

The bone putty preferably provides various other features in addition to filling a bone void or defect. For example, in some situations, it is important to provide a secure site for attachment of items such as bone screws. Because cancellous bone is very porous, it does not provide a secure foundation for the attachment of bone repair devices such as bone screws. It is also important that the defect filler be biocompatible and not cause any additional trauma at the surgical site.

Another desirable feature for bone putty is the ability to control bleeding during bone surgery. Earlier forms of bone putty, such as those based on bone wax, provide a useful hemostatic effect, but can interfere with subsequent healing of the bony tissues, and can also cause other problems such as inflammation.

Some existing bone putty materials include materials such as ceramics or demineralized bone matrix that help stimulate bone repair. However, including these materials can make the bone putty less viscous and less able to remain positioned inside the bone, and can also interfere with the ability of the bone putty material to fill in small bone pores. Accordingly, there remains a need for more effective bone putty materials that address one or more of the deficiencies of the bone putty materials that are currently available.

SUMMARY OF THE INVENTION

In one aspect, the present invention provides a bone pore or void filling composition. The composition includes a mixture of: a type I collagen and/or a type I collagen-glycosaminoglycan coprecipitate; a blend of polyethylene glycol polymers having different molecular weights; tricalcium phosphate; and bioactive glass. In some embodiments, the tricalcium phosphate comprises particles having a size from 50 to 300 microns. In additional embodiments, the tricalcium phosphate comprises from 15% to 30% by weight. In further embodiments, the bioactive glass comprises particles having a size from 50 to 300 microns. In additional embodiments, the bioactive glass comprises from 3% to 7.5% by weight.

In some embodiments, the blend of polyethylene glycol polymers in the composition consists of a first and a second polyethylene glycol polymer having different molecular weights. For example, in some embodiments, the first polyethylene glycol polymer has molecular weight within the range of 1350 g/mol to 1650 g/mol and the second polyethylene glycol polymer has a molecular weight within the range of 350 g/mol to 650 g/mol.

The bone pore or void filling composition includes a mixture of: a type I collagen and/or a type I collagen-glycosaminoglycan coprecipitate. In some embodiments the bone pore filling composition comprises a type I collagen, while in other embodiments, the bone pore filling composition comprises a type I collagen-glycosaminoglycan coprecipitate. In further embodiments, the weight percent of the type I collagen or the type I collagen-glycosaminoglycan coprecipitate is from 0.2% to 1.5%.

Another aspect of the invention provides a method of filling a bone pore or void, comprising administering a bone pore or void filling composition to the site of the bone pore or void. The composition includes a mixture of: a type I collagen and/or a type I collagen-glycosaminoglycan coprecipitate; a blend of polyethylene glycol polymers having different molecular weights; tricalcium phosphate; and bioactive glass.

The method includes various different methods of applying the composition to various different types of bone pores or voids. In some embodiments, the composition is manually applied to the bone pore or void, while in other embodiments the composition is applied to the bone pore or void using a syringe. In further embodiments, the composition is applied to a bone pore, or a plurality of bone pores, each having a diameter from 75 microns to 350 microns. In some embodiments, the composition is applied to a bone pore in spongy bone, while in other embodiments the composition is applied to a natural bone void. An advantage of the bone pore and void filling composition is that it is highly lubricative and quickly resorbs, leaving tricalcium phosphate and bioactive glass particles in the bone pores to induce and sustain bone growth.

Another aspect of the invention provides a bone pore or void filling kit. The kit includes a bone pore filling composition, comprising a mixture of: a type I collagen and/or a type I collagen-glycosaminoglycan coprecipitate; a blend of polyethylene glycol polymers having different molecular weights; tricalcium phosphate; and bioactive glass. The kit also includes a syringe for administering the bone pore filling composition; and a sterile package for holding the bone pore filling composition and the syringe. In some embodiments, the kit also includes instructions for filling a bone pore. The bone pore or void filling composition used can include any of the features described herein. For example, in some embodiments, the blend of polyethylene glycol polymers consists of a first and a second polyethylene glycol polymer having different molecular weights.

DETAILED DESCRIPTION OF THE INVENTION

Figure 1:
FIG. 1 provides an image of a bone putty implant placed within a rabbit leg.
Figure 2:
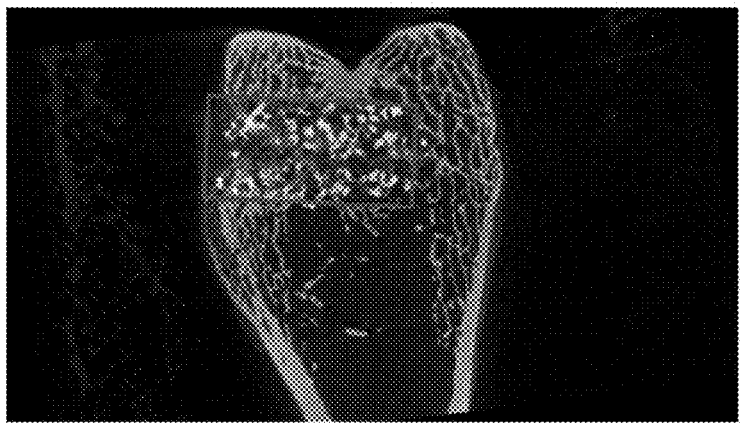
FIG. 2 provides images showing the results using MGP at 6 weeks for coronal and sagittal bone sections evaluated using microCT.
Figure 2:
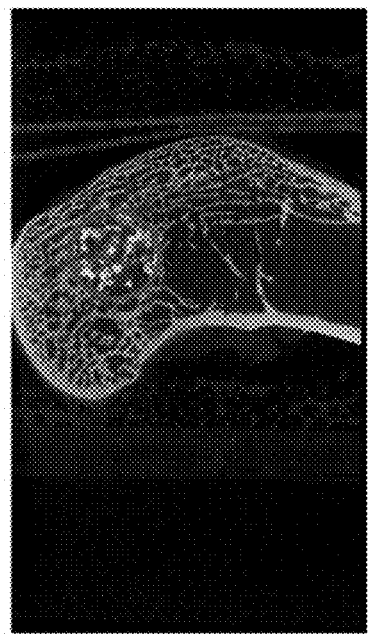
Figure 3:
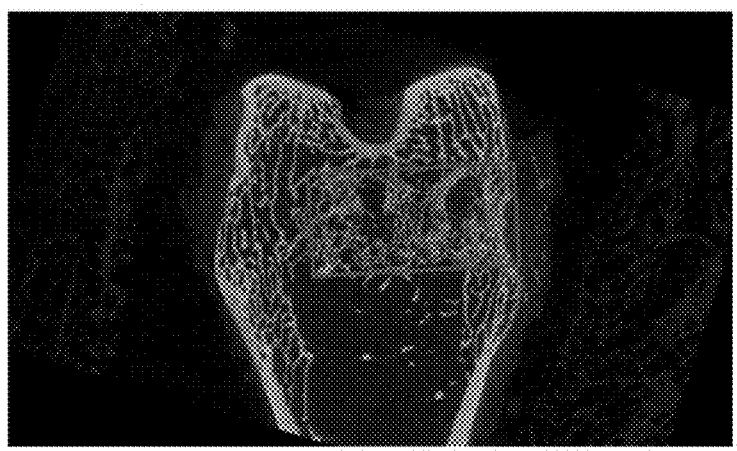
FIG. 3 provides images showing the results using Uni-FuZe-P at 6 weeks for coronal and sagittal bone sections evaluated using microCT.
Figure 3:
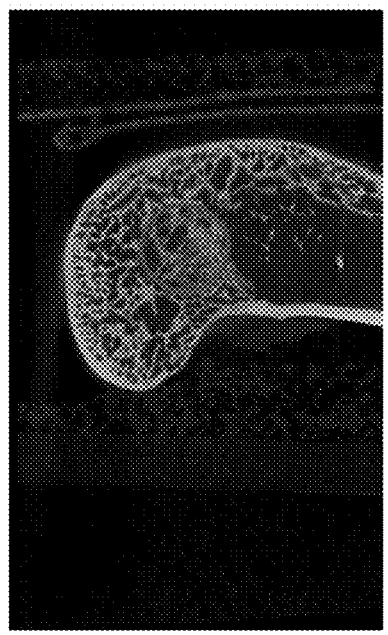
Figure 4:
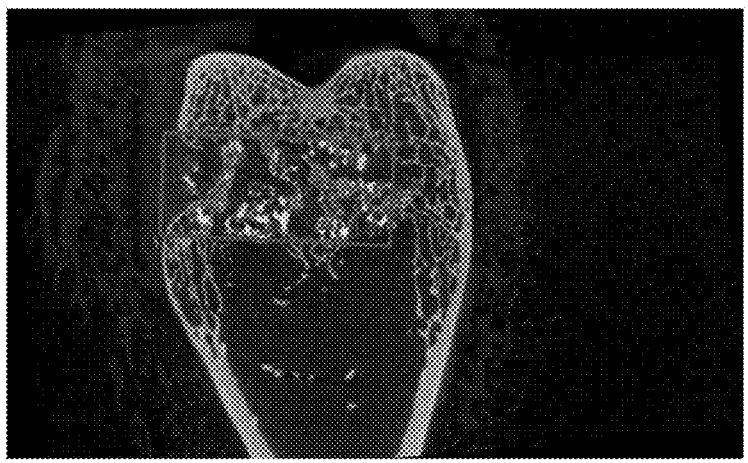
FIG. 4 provides images showing the results using MGP at 12 weeks for coronal and sagittal bone sections evaluated using microCT.
Figure 4:
Figure 5:
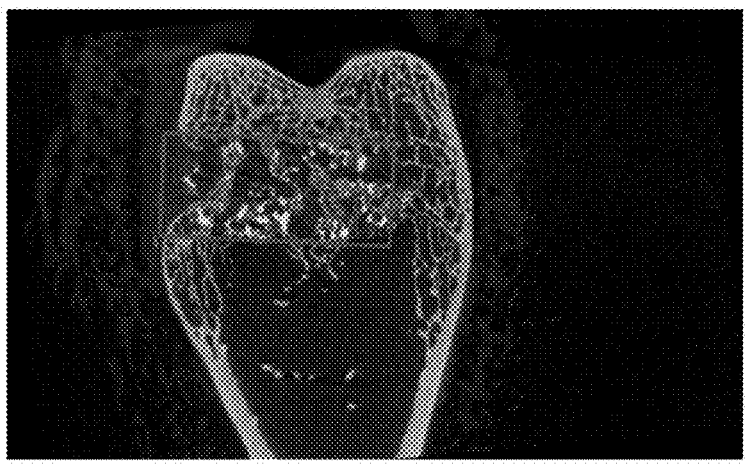
FIG. 5 provides images showing the results using Uni-FuZe-P at 12 weeks for coronal and sagittal bone sections evaluated using microCT.
Figure 5:

The present invention provides a composition for bone pore or void filling. The composition includes a mixture of:

a type I collagen and/or a type I collagen-glycosaminoglycan coprecipitate; a blend of polyethylene glycol polymers having different molecular weights; a bone growth stimulator; and bioactive glass. The invention also includes a kit for containing the bone pore or void filling composition, and methods for using the composition to fill a bone pore or void.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "comprises," "comprising," "includes," "including," "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The conjunctive phrase "and/or" indicates that either or both of the items referred to can be present.

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts at toxic concentrations, does not cause prolonged inflammation or irritation, or does not induce more than a basal immune reaction in the host.

As used herein, "putty" refers to a dough-like/clay-like composition that is readily malleable when pressure is applied, but which generally retains its shape when pressure is not being applied.

As used herein, "treatment" means any manner in which the symptoms of a defect, condition, disorder, or disease, or any other indication, are ameliorated or otherwise beneficially altered.

Bone Pore or Void Filling Composition

In one aspect, the present invention provides a bone pore or void filling composition. The composition includes a mixture of: a type I collagen and/or a type I collagen-glycosaminoglycan coprecipitate; a blend of polyethylene glycol polymers having different molecular weights; a bone growth stimulator; and bioactive glass. The bone pore or void filling composition has a putty consistency that provides many benefits such as enhanced cohesiveness, ease of handling and moldability. Because materials of the present invention are cohesive, they are also believed to provide the benefit of maintaining an active compound at the site of implantation longer than comparative materials with less cohesiveness.

Long bones are composed of a dense outer cortical bone (also called compact bone), which encloses an irregular medullary space or cavity containing cancellous bone. The cortical bone is a dense and compact bone that generally has a higher mineral content than cancellous bone and higher stiffness and strength. The cancellous bone (also called spongy bone or trabecular bone) is composed of a branching network of interconnecting bony trabecular elements (pores) and contains cells that have osteogenic potential.

When bone is damaged as a result of trauma (e.g., from accident or surgery), bone pores can be exposed as a result of the compact bone layer being damaged and exposing the lower spongy bone layer. The exposure of bone pores can create a problem with regard to bone repair, because the pores lack many of the features of cortical bone that contribute to bone repair. Compact bone is made of special cells called osteocytes that are lined up in rings around the canals, which together form osteons, which play a role in bone repair. Once exposed, it can be difficult for cortical bone to reform over the site of bone injury. In addition, porous bone is fragile and provides a poor attachment site for certain bone repair devices such as bone screws. Accordingly, there is a need to be able to fill bone pores with a material such as bone putty in order to facilitate bone healing and the attachment and integration of bone repair devices.

The bone pore or void filling composition includes a blend of polyethylene glycol polymers having different molecular weights. Polyethylene glycol is a polyether polymer, also known as polyethylene oxide and polyoxyethylene, depending on its molecular weight. Typically, this is the main material included in the bone pore and void filling composition, by weight. In some embodiments, the bone pore or void filling composition includes 50% to 90% polyethylene glycol by weight, while in other embodiments the composition includes 60% to 85% polyethylene glycol by weight, or 70% to 80% polyethylene glycol by weight.

In some embodiments, the blend of polyethylene glycol polymers consists of a first and a second polyethylene glycol polymer having different molecular weights. For example, the first polyethylene glycol polymer can have a molecular weight that is 2.5 to 3.5 larger than the molecular weight of the second polyethylene glycol polymer. In a further embodiment, the first polyethylene glycol polymer has a molecular weight within the range of 1250 g/mol to 1750 g/mol and the second polyethylene glycol polymer has a molecular weight within the range of 250 g/mol to 750 g/mol., while in an additional embodiment the first polyethylene glycol polymer has a molecular weight within the range of 1350 g/mol to 1650 g/mol and the second polyethylene glycol polymer has a molecular weight within the range of 350 g/mol to 650 g/mol, while in a yet further embodiment the first polyethylene glycol polymer has a molecular weight within the range of 1450 g/mol to 1550 g/mol and the second polyethylene glycol polymer has a molecular weight within the range of 450 g/mol to 550 g/mol.

The bone pore or void filling composition includes collagen and/or a type I collagen-glycosaminoglycan coprecipitate. Collagen is the major protein component of bone, cartilage, skin, and connective tissue in animals. Collagen occurs in several types, having differing physical properties. The most abundant types are Types I, II and III. Collagen derived from any source is suitable for use in the compositions of the present invention, including insoluble collagen, collagen soluble in acid, in neutral or basic aqueous solutions, as well as those collagens that are commercially available. Typical animal sources for collagen include but are not limited to recombinant collagen, fibrillar collagen from bovine, porcine, ovine, caprine, avian, and shark sources as well as soluble collagen from sources such as cattle bones and rat tail tendon. In some embodiments, the collagen is obtained from corium, which is a base material from which collagen is extracted.

Type I collagen is the most abundant collagen of the human body which forms large, eosinophilic fibers known as collagen fibers. The COL1A1 gene produces the pro-alpha1 (I) chain. This chain combines with another pro-alpha1(I) chain and also with a pro-alpha2(I) chain (produced by the COL1A2 gene) to make a molecule of type I procollagen. Type I collagen is present in scar tissue, as well as tendons, ligaments, the endomysium of myofibrils, the organic part of bone, the dermis, the dentin and organ capsules.

The collagen included in the bone pore and void filling composition can be in the form of small flakes, particles, or fibers. Small flakes or particles can be obtained by milling a collagen sponge, or other form of collagen having a reticulated cellular structure. For example, in some embodiments, the collagen comprises fine flakes or particles obtained by milling collagen through a 10, 20, or 30 mesh screen. A preferred size is obtained by milling collagen through a 20 mesh screen.

The collagen included in the bone pore or void filling composition can be type I collagen and/or a type I collagen-glycosaminoglycan coprecipitate. In some embodiments, where both are present, the ratio of type I collagen to type I collagen-glycosaminoglycan coprecipitate ranges from about 0.5:1 to about 2:1. In further embodiments, the ratio of type I collagen to type I collagen-glycosaminoglycan coprecipitate ranges from about 0.8:1 to about 1.5:1. In further embodiments, the type I collagen is present in a ratio of about 1:1 compared with type I collagen glycosaminoglycan coprecipitate.

The amount of type I collagen and/or type I collagen-glycosaminoglycan coprecipitate included in the bone pore and void filling composition can vary from about 0.1% to about 10% by weight. In some embodiments, the composition includes from 0.1% to 5% collagen and/or type I collagen-glycosaminoglycan coprecipitate by weight, in further embodiments, the composition includes from 0.2% to 1.5% collagen and/or type I collagen-glycosaminoglycan coprecipitate by weight, in yet further embodiments, the composition includes from 0.3% to 1% collagen and/or type I collagen-glycosaminoglycan coprecipitate by weight.

The bone pore and void filling composition can also include a type I collagen-glycosaminoglycan coprecipitate. The type I collagen-glycosaminoglycan coprecipitate is formed when collagen is precipitated from acid dispersion by addition of a GAG such as chondroitin 6-sulfate. The relative amount of GAG in the coprecipitate varies with the amount of GAG added and with the pH. Yannas et al., J Biomed Mater Res., 14(2):107-32 (1980). The coprecipitate is predominantly collagen. In some embodiments, the type I collagen glycosaminoglycan coprecipitate comprises a ratio of glycosaminoglycan to type I collagen from between 1 to 8 and 1 to 15. In further embodiments, the type I collagen glycosaminoglycan coprecipitate comprises a ratio of glycosaminoglycan to type I collagen from between 1 to 10 and 1 to 12. In some embodiments, the ratio is about 1 to 11.

The term glycosaminoglycan (GAG) describes hexosamine-containing polysaccharides. Glycosaminoglycans are also referred to as mucopolysaccharides. Chemically, GAG are alternating copolymers made up of residues of hexosamine that are glycosidically bound and alternating in a more or less regular manner with either hexuronic acid or hexose moieties. Glycosaminoglycans can be obtained from various marine and mammalian sources.

Examples of glycosaminoglycan molecules that can be included in the bone pore or void filling composition include hyaluronic acid and chondroitin sulfate. Various forms of GAG which may be suitable for use in the bone pore or void filling composition include, but are not limited to, hyaluronic acid, chondroitin 6-sulfate, chondroitin 4-sulfate, heparin, heparin sulfate, keratin sulfate and dermatan sulfate. In some embodiments, the glycosaminoglycan included in the bone repair composition is chondroitin 4 sulfate or chondroitin 6 sulfate.

The bone pore or void filling composition also includes a bone growth stimulator (e.g., tricalcium phosphate). In some embodiments, the bone growth stimulator (e.g., tricalcium phosphate) comprises from 5% to 50% by weight, from 10% to 40% by weight, from 15% to 30% by weight, or from 15% to 25% by weight.

Suitable bone growth stimulators include substances that can enhance filling of the bone pore or voids and encouraging integration and regrowth of surrounding bone. Some examples of bone growth stimulators include, but are not limited to, calcium, hydroxyapatite, tricalcium phosphate, chitosan, coral derivatives, bone growth factors, such as for example bone morphogenic proteins, and the like. Hydroxyapatite includes $Ca_{10}(PO_4)_6(OH)_2$, and is exogenous calcium phosphate that resembles the primary inorganic component of bone. This agent provides an osteophillic matrix for bone to bond and grow. A preferred bone growth stimulator for inclusion in the bone repair composition is tricalcium phosphate $(Ca_3(PO_4)_2)$. This term also includes sources or variants of tricalcium phosphate, such as bone ash, alpha or beta tricalcium phosphate, and combinations thereof.

The bone growth stimulator (e.g., tricalcium phosphate) is included in the bone pore and void filling composition as small particles. Preferably, the particles have a size that allows them to readily fit within bone pores. In some embodiments, the particles have a size from 10 to 1000 microns. In other embodiments, the particles have a size from 25 to 500 microns. In further embodiments, the particles have a size from 50 to 300 microns. In yet further embodiments, the particles have a size from 50 to 200 microns. In additional embodiments, the particles have a size from 100 to 200 microns.

The bone pore and void filling composition also includes bioactive glass. Bioactive glass is glass that is glass that undergoes specific surface reactions when implanted into a subject that facilitates integration and biocompatibility of the material. For example, in some embodiments the bioactive glass develops a hydroxyapatite surface layer upon implantation that facilitates the formation of a firm bond with hard and soft tissues. Bioactive glass is commercially available from companies such as Prosidyan® and the Mo-Sci Corporation. Bioactive glass is based on Silicon Dioxide ($SiO_2$) but also typically includes lesser amounts of Calcium Oxide (CaO), Sodium Oxide ($Na_2O$), and Phosphorus Pentoxide ($P_2O_5$)

Embodiments of the bone pore and void filling composition can include varying amounts of the bioactive glass. In some embodiments, the bone pore and void filling composition includes from 1% to 15% bioactive glass by weight. In other embodiments, the bone pore and void filling composition can include 1% to 10% bioactive glass by weight. In other embodiments, the composition includes from 2% to 10% bioactive glass. In other embodiments, the composition includes from 3% to 7.5% bioactive glass, while in further embodiments, the composition includes from 4% to 6% bioactive glass.

The bioactive glass is included in the bone pore and void filling composition as small particles. Preferably, the particles have a size that allows them to readily fit within bone pores. In some embodiments, the bioactive glass and the tricalcium phosphate particles will be selected to have the same size. In some embodiments, the particles have a size from 10 to 1000 microns. In other embodiments, the particles have a size from 25 to 500 microns. In further embodiments, the particles have a size from 50 to 300 microns. In yet further embodiments, the particles have a size from 50 to 200 microns. In additional embodiments, the particles have a size from 100 to 200 microns.

The pH of blood plasma typically is 7.3 to 7.4. Thus, it is preferable to maintain the pH of the bone pore and void filling composition, which is in intimate contact with blood, at a biocompatible pH 7.2-7.4. The pH of the bone pore or void filling composition can be adjusted using various buffers known to those skilled in the art, such as a phosphate buffer. It is important to note that the body has many complex and redundant mechanisms to maintain its biochemical balance. The blood pH can be adjusted by several means to its normal, physiologic pH. Hence the presence of a bone putty at the site of a bleeding bone wound will eventually be overcome and any non-biocompatible condition will return to normal pH. However, it is preferable that the bone putty start out and maintain physiologic pH without stressing the body's biochemical mechanisms when the bone pore or void filling composition is applied at the site of the bone void or pores.

The bone pore and void filling composition can further comprise bioactive molecules to facilitate bone repair or have other beneficial effects. Suitable bioactive molecules include, but are not limited to, growth factors, anti-inflammatory agents, wound healing agents, anti-scarring agents, antimicrobial agents (for example, silver), cell-adhesion peptides including Arg-Gly-Asp (RGD) containing peptides, nucleic acids, nucleic acid analogues, proteins, peptides, amino acids, and the like, or combinations thereof.

In some embodiments, the bone pore or void filling composition further comprises a hemostatic agent. Hemostatic agents include, but are not limited to, prothrombin, thrombin, fibrin, fibronectin, Factor X/Xa, Factor VII/VIIa, Factor IX/IXa, Factor XI/XIa, Factor XII/XIIa, factor XIII, factor VIII, vitronectin, tissue factor, proteolytic enzyme obtainable from snake venom such as batroxobin, von Willebrand Factor, plasminogen activator inhibitor, platelet activating agents, synthetic peptides having hemostatic activity, collagen particles, derivatives of the above or any combination thereof. These hemostatic agents can enhance clotting. In some embodiments, the hemostatic agent comprises gelatins, collagens, oxidized celluloses, thrombin and fibrin sealants, chitosan, synthetic glues, glutaraldehyde-based glues, or a combination thereof. In addition, it should be noted that collagen particles can also provide a hemostatic effect.

The bone pore and void filling composition can be treated to sterilize or to reduce bioburden of the material. For example, sterilization procedures can include low dose irradiation, antibiotic washing and physical debridement. These methods provide the benefit of reducing antigenicity as well as sterilizing the bone pore and void filling composition. More extensive sterilization can be provided through gamma irradiation, electron beam irradiation, or ethylene oxide treatment.

Processes for producing bone pore or void filling compositions as a putty are not generally limited and include those methods known in the art. In one embodiment, the components (i.e., the type I collagen and/or a type I collagen-glycosaminoglycan coprecipitate; a blend of polyethylene glycol polymers having different molecular weights; tricalcium phosphate; and bioactive glass) are combined. In some embodiments, the polyethylene glycol polymers are combined first by, for example, blending them in a jacketed mixer. The polyethylene glycol polymers can then be melt blended, after which the tricalcium phosphate and bioactive glass are introduced. The mixture is then quenched. The mixed/quenched putty can then be expressed into open ended syringes or otherwise packaged for later use. As a putty, the composition desirably has suitable rheological properties (e.g., viscosity) so as to be injectable through applicators including large gauge applicators, such as catheters, or syringes, while largely remaining at the implant site.

Methods of Filling a Bone Pore or Void

Another aspect of the invention provides a method of filling a bone pore or void. The method includes administering a bone pore or void filling composition, as described herein, to the site of a bone pore or void. When being applied to bone pores, the composition is typically applied to a bone pore in spongy bone, which is significantly more porous than compact bone. The putty is gently packed in these areas without required hydration.

The bone pore or void filling composition can be applied to bone pores and/or bone voids. Bone pores are small holes that form a network of channels within the bone. The pores serve to reduce the weight of the bone, while maintaining structure and allowing vascularization. Bone pores can range in size from 10 μm to 600 μm. Typically, cancellous bone (i.e., spongy bone) has 75-85% porosity with 300-600 μm diameter pores, while cortical bone (i.e., compact bone) has 5-10% porosity with 10-50 μm diameter pores. It is preferable that the particles of bone growth stimulator (e.g., tricalcium phosphate) and bioactive glass included in the bone putty composition have a size smaller than the pores so that they can fill the pores while providing a smooth surface for bone regrowth. In some embodiments, the bone pores have a diameter of 50 to 400 microns, while in other embodiments the bone pores have a diameter from 75 microns to 350 microns, while in further embodiments the bone pores have a diameter from 100 to 200 microns.

When the bone pore or void filling composition is applied to a bone pore, it is typically applied to a plurality of bone pores present in an area of bone. The bone putty is applied over at least a portion of an area of bone including a plurality of bone pores. Typically, the area is an area of spongy bone that has been exposed as a result of disease, injury, or surgery. When applied to such an area, the bone putty is typically applied in a thin layer to cover the area including bone pores. The small particle size of the bioactive glass and bone growth stimulator (e.g., tricalcium phosphate) allows the particles to settle within the pores, increasing the smoothness and the effectiveness of the resulting layer.

In some embodiments, the composition is manually applied to the bone pore or void. For example, the bone pore and void filling composition can be applied using the finger of an individual who is operating on the subject having bone pores or voids that need to be filled. The blend of polyethylene glycol polymers is temperature sensitive, and manual application provides sufficient body heat to activate the putty to become more grease-like for application. Bone pore or void filling composition can be administered directly to the site of the bone pore or void. For example, the bone repair composition can be packed into bony voids. In some embodiments, the bone repair composition can be molded or formed into a desired shape generally conforming to the shape and size of the defect site, and then positioned or pressed, either manually and/or using instrumentation, into the defect site.

Before application, the "putty" substance may be beaten or kneaded to the consistency of dough, and manipulated into a shape closely approximating that of the repair site. Putty provides ease of use and economy of product manufacture. Putties are desirable for surgical bone repair as they can be easily delivered to difficult surgical sites and molded in situ into desired shapes. These products are desirable for the reconstruction of skeletal defects, e.g., in spine, dental, and/or other orthopedic surgeries.

In some embodiments, the composition is applied to the bone pore or void using a syringe. The bone putty or void filling composition is readily malleable and injectable. "Injectable" refers to the ability of bone pore or void filling compositions to be introduced at a repair site under pressure (as by introduction using a syringe or other cannulated device). Examples of suitable syringes include the Merit 20SL open end syringe, and the Merit Closed end syringe, available from MERITMEDICAL®. If the composition is injectable, the composition may be loaded into the barrel of a disposable syringe, with or without a cannula (e.g., needle) attached, and is extruded through the barrel aperture to the desired anatomical site. An injectable composition of the present invention may, for example, be introduced between elements or into a confined space in vivo (e.g., between pieces of bone or into the interface between a prosthetic device and bone, into a tooth extraction socket, into alveolar ridge/sinus cavity, into a confined void with any geometry due to trauma created either natural or surgical procedure, into vertebral interbody spaces, spinal fusions, joint and trauma defects, bone fractures. An injectable composition may also be used to fill bone cysts, tumors and other well-delineated voids In accordance with the methods of the invention, a defect site is desirably prepared to expose healthy bleeding bone, facilitating subsequent bone growth. The methods may be performed using minimally invasive procedures known to one skilled in the art. The methods may be used in at least partially filling bone pores or voids of the skeletal system. Such applications include induction of bone formation for hip replacement operations, knee replacement operations, spinal fusion procedures, repair of periodontal defects, treatment of osteoporosis, repair of bone tumor defects, dental procedures, repair of cranial maxilla facial defects, and repair of bone fractures or defects. The pores or voids may be a result of a development failure, degeneration or trauma, either natural or by surgical creation. The bone pore or void filling composition is resorbed by the body during the healing process (over days, weeks, and months).

The bone pore or void filling composition can be used to promote bone growth and/or bone remodeling, including in the treatment of any of a variety of bone diseases, disorders, defects or injuries for which other bone grafts, including allografts or autografts, have been employed. Such diseases, disorders, defects or injuries are well known to a skilled artisan. The subject for treatment can be any animal subject that has a bone disease, disorder, defect or injury and is in need of treatment, including any mammal, such as a human or non-human primate. In particular examples, the subject is a human. The bone pore or void filling composition can be used to fill or partially fill areas including bone pores or bone voids and/or gaps of the skeletal system associated with the bone disease, disorder, defect or injury.

In some embodiments, the bone putty composition is applied to a bone void. Bone voids are gaps in the bone structure that are significantly larger than bone pores, and are typically the result of trauma or surgery on the bone. For example, the bone pore or void filling compositions described herein can be used to correct bone defects in orthopedic, neurosurgical plastic or reconstructive surgery, in periodontal procedures, and in endodontic procedures. Such applications include, but are not limited to, induction of bone formation for hip replacement operations, knee replacement operations, foot and ankle surgeries (e.g. ankle fusion), spinal fusion procedures, repair of periodontal defects, treatment of osteoporosis, repair of bone tumor defects, dental procedures, repair of cranial maxilla facial defects and repair of bone fractures or defects. The bone disease, disorder, defect or injury can result from a developmental failure, or by degeneration or trauma, caused naturally or by surgery. In some embodiments, the composition is applied to a natural bone void, which is a bone void which is caused naturally.

In some examples, the bone pore or void filling composition can be used in conjunction with devices employed in the treatment of bone diseases, defects, disorders and injuries, such as, for example, orthopedic cage implants, bone screws, ceramics or plates that can be employed in the spine or in bones to promote bone growth and fusion. Furthermore, the bone pore or void filling composition can be used in conjunction with an autologous bone graft.

Bone Pore and Void Filling Kits

Another aspect of the invention provides a bone pore or void filling kit. The kit includes a bone pore filling composition, comprising a mixture of: a type I collagen and/or a type I collagen-glycosaminoglycan coprecipitate; a blend of polyethylene glycol polymers having different molecular weights; a bone growth stimulator; and bioactive glass; a syringe for administering the bone pore filling composition; and a sterile package for holding the bone pore filling composition and the syringe. The bone pore or void filling composition can include any of the bone pore or void filling compositions described herein. For example, in some embodiments, the bone pore or void filling composition includes a blend of polyethylene glycol polymers consists of a first and a second polyethylene glycol polymer having different molecular weights. Kits may include one, two, three or four receptacle-containers, one of which may be suitable for combination and/or "hydration" of the components. The kit may further have a mixing implement such as a spatula, stir rod, etc., a disposable syringe barrel with or without a cannulated extension (e.g., a needle) in which to place and deliver the mixed bone pore or void filling composition.

In addition to the above components, the subject kits may further include (in certain embodiments) instructions for filling a bone pore or bone void using the bone pore or void filling composition. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), hard drive etc., on which the information has been recorded. Yet another form of these instructions that may be present is a website address which may be used via the internet to access the information at a removed site.

As used herein, the term "package" refers to a solid matrix or material such as glass, plastic, paper, foil and the like capable of holding the bone repair composition. For example, in some embodiments, the package comprises high density polyethylene. Preferable the package is transparent in order to allow the bone repair composition to be viewed from outside the package. In some embodiments, the package includes a tray that includes one or more grip regions to facilitate access to the bone repair composition. The package should be sterilized before use to provide a sterile package. The package can be sterilized after the bone pore and void filling composition and the syringe have been included within the package to assure that these components are sterile as well.

The present invention is illustrated by the following examples. It is to be understood that the particular examples, materials, amounts, and procedures are to be interpreted broadly in accordance with the scope and spirit of the invention as set forth herein.

EXAMPLES

Example 1: Bone Putty Biocompatibility

A variety of different tests were conducted to evaluate the biocompatibility of the bone putty described herein. The bone putty that was evaluated included 4.67 grams of PEG 1450, 2.33 g of PEG 600, 2.40 g of tricalcium phosphate, 0.60 g of bioactive glass, and 0.10 g of collagen, which were mixed to form a putty as described herein. Tests were conducted to evaluate the cytotoxicity, sensitization, irritation, acute systemic injection, material-mediated pyrogenic effects, and implantation at 4 weeks.

Cytotoxicity

MEM Elution testing was performed by Nelson Laboratories according to ISO 10993-5: *Biological evaluation of medical devices—Part 5: Tests for In Vitro cytotoxicity*. The purpose of this test is to evaluate the presence of potential toxicants released from the device when in its final and sterilized form. Based on the criteria outlined in the standard, devices are considered cytotoxic if they score greater than 2 on the reactivity scale. The device was extracted with agitation in 1×MEM with 5% bovine serum at 37° C. for 72 hours at a ratio of 0.2 g/mL. Cell culture 6-well plates, seeded with L-929 cells, were incubated with the unfiltered, neat extract of the test article. Incubations were maintained at 37° C. for 48 hours with 5% $CO_2$. The cells were then studied under a microscope to determine the level of cytotoxicity. Scores were given from 0-4: "0" being no cell lysis and "4" being nearly complete cell destruction. The neat sample of the subject device extract demonstrated a cytotoxic reaction in the in vitro test system with a score of "4". Based on acceptance criteria, the device is therefore considered cytotoxic.

The cytotoxicity test is a useful biocompatibility test for possible toxic leachables from material or residual processing. It is also historically the most sensitive test available and is used as a screening test for materials, process residuals, and the final device configuration. This test is used to determine toxic effects of the device on a cellular level and can help predict the potential clinical response. In the ANSI/AAMI/ISO 10993-5 Guidance section 10 it states "Any cytotoxic effect can be of concern. However, it is primarily an indication of potential for in vivo toxicity and the device cannot necessarily be determined to be unsuitable for a given clinical application based solely on cytotoxicity data." When elevated cytotoxicity results are seen, a risk assessment should be performed to identify the risk. Then a risk assessment should look at the toxic potential of the material or compound to determine the clinical impact. The investigation should include a review of the procedures to determine the effectiveness of the test system, additional testing to evaluate clinical risk of the results, and then a clinical risk assessment of the toxicity using additional animal testing along with chemical analysis and analysis of compounds.

The materials included in the Bone Putty, polyethylene glycol, tri-calcium phosphate and porous bioactive glass, are all known to be biocompatible and are often used in the formulation of bone void fillers. All the in vivo tests performed on the Bone Putty which demonstrate a more clinically relevant application and overall effect of the Bone Putty than an in vitro cell culture test such as the MEM elution assay, showed no evidence of device-related toxic effects. Moreover, the performed E&L testing and accompanied toxicological risk assessment addressed any concern for any chemical compounds detected in the extract of the Bone Putty and identified that the toxicological risk to the patient is considered to be low.

Thus, based upon examination of the Bone Putty, history of use of the included materials in medical industry, other more clinically relevant biological endpoints with passing results as well as the performed chemical characterization with a toxicological risk assessment, this cytotoxicity failure may not be clinically relevant and adverse effects in patients are considered to be unlikely.

Sensitization

Testing was performed by Toxikon USA according to ISO 10993-10: Biological evaluation of medical devices—Part 10: Tests for irritation and skin sensitization. The purpose of the study is to determine the potential allergenic or sensitizing capacity of the test article. Sensitization testing is conducted in two phases: induction and challenge. The induction phase has two applications: injection (on Day 0) and topical (on Day 7). Based on the criteria outlined in the standard, a device is considered sensitizing if it achieves a score of ≥1 on the Magnusson and Kligman grading scale. Additional sensitization classification or grading scale per USP is used to define the allergenic potential of the test article based on the number of responsive animals with observed skin reactions at any given time point. The material was extracted in Normal Saline (NS) or Cottonseed Oil (CSO) at 50° C. for 72 hours at a ratio of 0.2 g/mL. Ten test and five control guinea pigs were injected per extract vehicle with three pairs of 0.1 mL intradermal injections made in a row on each side of the midline. The first pair of injections included a 1:1 (v/v) mixture of Freund's Complete Adjuvant (FCA) with the appropriate solvent/vehicle, the second pair of injections includes the appropriate solvent/vehicle with or without the extracted test article, and the third pair of injections is performed with 1:1 (v/v) mixture of FCA with either the test article extract in an appropriate solvent/vehicle or just the solvent/vehicle. FCA is used to potentiate the sensitization reaction and to evaluate the possibility of hyperreactive skin status during the test and thus interference with the reading and scoring. On Day 6, the injection site area was clipped free of fur and treated with 10% (w/w) sodium lauryl sulfate (SLS) in petrolatum that acts to increase the dermal response to weak sensitizers. On day 7 after injection, filter paper saturated with fresh test extract was secured to the skin of each test animal and filter paper saturated with fresh control vehicle was secured to the skin of each control animal and left there for 48 hours. On day 23 after injection, filter paper was again saturated with fresh test extract or control vehicle. A control vehicle patch was attached to the left flank of each animal and test extract patch was attached to the right flank of each animals. The patch was left there for 24 hours and scoring was performed at 24, 48 and 72 hours after the patch was removed. The evaluation of skin reactions used the four-point Magnusson and Kligman grading scale, and the allergenic potential of the test article was classified based on the percent of responsive animals with any skin reaction score of 1 or greater at any time point. The test group demonstrated no visible change in dermal observations with 0% animals sensitized for both NS and CSO extracts. Based on the USP grading, and the calculated allergenic potential of the test article, the device is categorized as a non-sensitizer.

Irritation

Testing was performed by Toxikon USA according to ISO 10993-10: Biological evaluation of medical devices—Part 10: Tests for irritation and skin sensitization. The purpose of this test is to determine the potential irritation effects of the test article extract as a result of an intracutaneous injection to evaluate whether the device stimulates a local irritation response in the dermal tissues. Based on the criteria outlined in the standard, a device is considered an irritant if the comparative result (the average score of the test animals, minus the average score of the control animals) is greater than 1. The device was extracted in NS or CSO at 50° C. for 72 hours at a ratio of 0.2 g/mL. A volume of 0.2 mL per site of one extract was injected intracutaneously at one side of each three rabbits, with fine sites for the test article extract and five posterior sites for the control. Similarly, at the other side of each rabbit, the other test extract was injected. Appearance of each injection site was observed for signs of erythema and edema, and scored based on the classification system for scoring skin reactions immediately following injection, and at 24, 48, and 72 hours post injection. The overall mean score difference between the control and the test article were 0.0 for both NS and CSO extracts. The device is therefore considered a non-irritant.

Material Mediated Pyrogen

Testing was performed by Toxikon USA according to the United States Pharmacopeia (USP) Pyrogen Test Procedure. The purpose of the study was to determine the potential presence of chemical pyrogens in the extracts of solid materials in order to limit to an acceptable level the risks of febrile reaction following administration of the product to the patient. The study involved measuring the rise in temperature of rabbits following the intravenous injection of the test article extract. The test article was extracted in 0.9% NS at 50° C. for 72 hours at a ratio of 0.2 g/mL. The test extract was injected into the marginal ear vein of each of the three animals; additionally, one animal was injected with the vehicle control. All animals received a 10 mL/kg dose of the test article. Rectal temperatures were recorded for each animal prior to injection and between 1 and 3 hours post-injection at 30 minute intervals. During the 3 hour observation period, none of the rabbits administered with the test article extract had a temperature rise ≥0.5° C. at the required observation time points. This response did not exceed the USP limit and meets the requirements for this test. Therefore, these results indicate that the test article was determined to be non-pyrogenic.

Acute Systemic Toxicity

Testing was performed by Toxikon USA according to ISO 10993-11: Biological evaluation of medical devices—Part 11: Tests for systemic toxicity. The purpose of this study was to determine the potential toxic effects of the test article extract as a result of a single-dose systemic injection in mice. The device was extracted in NS or CSO at 50° C. for 72 hours at a ratio of 0.2 g/mL. The NS test article and control extracts were injected intravenously into five mice each. The CSO test article and control extracts were injected intraperitoneally into five mice each. Clinical observations and body weight recordings were taken before injection as well as 24, 48, and 72 hours after injection. Based on the criteria outlined the standard, a device is considered toxic if death in two or more mice occurs or other toxic signs such as convulsions, prostration, or body weight loss greater than 10% in three or more mice. At the 4-hour time point NS test animal #3 was found dead. A gross necropsy was performed with no abnormal findings. None of the other test or control animals exhibited overt signs of toxicity at any of the observation time points. Per Section 9.2 of the report "A gross necropsy was performed with no abnormal findings". Based on this and the fact that the rest of the test animals were normal throughout the duration of the test, the testing facility determined that the death of one test animal during the study was an isolated event and does not reflect the effect of the test article on the animal. The device was therefore considered non-toxic.

4 Week Bone Implantation

Testing was performed by American Preclinical Services (APS) according to ISO 10993-6: Biological evaluation of medical devices—Part 6: Tests for local effects after implantation. Implantation study for the Bone Putty included five test animals, each receiving two test articles in one tibia, and two control articles in the other tibia. The standard requires that a minimum of three animals are to be used. Implants should be planned to obtain 10 control and 10 test article implant sites for examination. At the completion of the study, all of the animals on study were euthanized and necropsy was performed for target tissue procurement. Implant sites were explanted, fixed, and embedded. The embedded specimens underwent histopathological interpretation to evaluate cell type presence and tissue response to test and control articles. Clinical, macroscopic and microscopic observations were also made throughout the study.

There were no signs of infections associated with any of the implant sites. All animals were in overall good health over the course of the study except for one animal, which exhibited an approximately 0.5-1.0×1.0 cm soft swelling on the medial ventral abdomen during study days 2-28. There were no notable gross findings, no abnormalities observed in four out of five animals. One animal exhibited multifocal smooth, firm white subcutaneous masses at one set of implant sites and smooth, purple intramuscular discoloration at the other set of implant sites. These appeared to be related to the surgical procedure. Per the pathology report, the test articles implant sites had narrow to moderately thick bands of fibrous connective tissue containing few fibrocytes, whereas the control sites had narrow to thick bands of fibrous connective tissue containing few fibrocytes. There were rare to mild multifocal infiltrates of inflammatory cells composed primarily of macrophages at test article implant sites. Minimal multifocal neovascularization was noted in two out of nine sections examined in the test articles sites; in control sites, minimal to mild multifocal neovascularization was noted in two out of ten sections examined. Necrosis and fatty infiltration was not noted in any the examined sections for test article and control sites. The conclusion of the study is based on the scores assigned by the pathologist during the microscopic evaluation. The average irritancy score per implant site was evaluated as 5.8 for the control site and 5.1 for the test site. The resulting overall irritant ranking score for the 4 week implant study indicates the test article is considered to have a minimal or no reaction to the tissue. Detailed information on the scores and scoring criteria are contained in the final report.

It should be mentioned that only nine test article implanted sites were scored, which is a deviation from the standard that required 10 sites to be scored. It is noted in the report that while all 10 test implant sites were identified and recovered, one of the test Implant sites was not available for evaluation. The nine evaluable test slides, however, afforded the study pathologist an accurate overall evaluation. Thus, even though the standard requires the analysis of 10 test article site, since the nine evaluated sites showed consistent low tissue reactivity, the results obtained in the study are considered valid for the test article.

Example 2: Bone Putty Efficacy

The current study examined the in vivo performance of two bone void filler materials, Uni-FuZe-P and Mastergraft Putty (predicate material) in an established rabbit femoral defect model. Uni-FuZe-P is the same bone putty composition of the present invention which was also used for the biocompatibility studies described in Example 1. More specifically, it was a bone putty composition that included 4.67 grams of PEG 1450, 2.33 g of PEG 600, 2.40 g of tricalcium phosphate, 0.60 g of bioactive glass, and 0.10 g of collagen, The test groups were evaluated for biocompatibility and osteoconductive healing response using radiographic, microCT and histological analyses at time points of 1 day, 6, and 12 weeks following surgery.

Surgical Prep: All animals were prepared for surgical procedures as per BHRL/ISRC/ARS SOPs. After the pre-anesthetic had taken effect, rabbits were clipped free of fur over the surgical areas. The surgical areas were scrubbed with chlorhexidine soap and wiped with isopropyl alcohol. Betadine solution was applied just prior to surgical incision.

A lateral incision, approximately 2.0 centimeters long, was made and the soft-tissues overlying the femoral condyle dissected. A 5.0 mm drill bit was used to drill through the cortex to a depth of 10 mm and bone removed. Drilling was done under constant saline irrigation. Once bone was removed, graft material was hand-packed into the defect to the level of the original cortex (~0.2 cc) or left empty. Fascia and skin were closed in the routine manner consistent with good surgical practice. This surgical procedure was conducted on the contralateral limb as well. FIG. 1 provides an image of the implant placed within a rabbit leg.

No complications were observed in either test groups over the course of the study. Gross observations of the implant sites demonstrated healthy tissue absent of adverse inflammatory reactions regardless of test group or time point. Radiographic analysis indicated no adverse reactions and a normal progression in healing over time in both groups. MicroCT scans supported the radiographic observations, similar osteoconductive healing response in both groups, with a progression of new bone formation and implant resorption observed over time.

Ventral/dorsal and lateral radiographs were obtained with a Simon DR (Quantum) RAD-X High Frequency Radiographic Imaging System, (model: E7242X), and stored using Whitecap PACs system. Radiographic images were obtained postoperatively and at 1 day, 6, and 12 weeks post-surgery. Animals received sedation as described for surgical procedures in Section 6.8 prior to radiography. Radiographs were examined to confirm graft placement and assess graft migration, osteolysis, fracture, and/or any other adverse events.

Animals were euthanized using Euthasol solution (120 mg/kg IV). Necropsy was conducted on all study animals according to BHRL/ISRC standard operating procedures under the supervision of the PI. Necropsy included examination of the external surface, all orifices, thoracic, abdominal, and pelvic cavities including contents. The stifle joint was transected removing the tibia. The soft tissues were removed from the femoral condyles and a saw was used to cut the femur just proximal to the condyles (approximately 20 mm from the joint surface). Condyles from the left and right limbs were placed in 10% neutral buffered formalin.

Each specimen was scanned using a SkyScan 1176 Micro-CT. Microtomography uses a similar technique as computerized tomography systems in medicine (MDCT-scans) but at a higher resolution (as thin as 9 µm). X-ray images (2D) were acquired in multiple planes while either the sample or the source/detector pair was rotated. Internal structures were reconstructed as a series of 2D cross sections which were then used to analyze the two and three dimensional morphological parameters of the specimen. Image acquisition and Reconstruction parameters are shown in Table 6.3. The SkyScan 1176 was calibrated according to the manufacturers recommended schedule for contrast, positioning and density. Each specimen was analyzed for Total Volume (TV), Bone Volume (BV), Graft Volume (GV), Soft Tissue Volume (SV). Soft Tissue Volume includes both general soft tissues and void space not detected as bone or implant (threshold: <58).

The test groups were comparatively evaluated for host response, new bone formation and implant resorption within the healing defects using radiographic, microCT and histological analyses at time points of 1 day, 6 weeks, and 12 weeks. Gross observations of the implant sites demonstrated healthy tissue absent adverse inflammatory reactions regardless of test group or time point. Radiographic analysis indicated no adverse reactions and a normal progression in healing over time in both groups. MicroCT scans supported the radiographic observations, demonstrating no adverse reactions and a similar osteoconductive healing response in both groups, with a progression of new bone formation and implant resorption over time. The results of the microCT scans are shown in FIGS. 2-5. Uni-FuZe-P was demonstrated to be osteoconductive, providing a scaffold for cell attachment and supporting formation of osseous tissue across bony defects.

This study has confirmed the biocompatibility and normal osteoconductive healing response associated with the Uni-FuZe-P and has demonstrated equivalent in vivo performance to the Mastergraft Putty across radiographic, microCT and histological endpoints in an established femoral cancellous defect animal model.

The complete disclosure of all patents, patent applications, and publications, and electronically available materials cited herein are incorporated by reference. Any disagreement between material incorporated by reference and the specification is resolved in favor of the specification. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A bone pore or void filling composition, comprising a mixture of:
    a collagen component comprising a type I collagen and/or a type I collagen-glycosaminoglycan coprecipitate;
    a polyethylene glycol component comprising a blend of polyethylene glycol polymers having different molecular weights, wherein the blend of the polyethylene glycol polymers comprises 55% to 90% by weight of the composition;
    a calcium phosphate component comprising tricalcium phosphate; and
    a glass component comprising bioactive glass,
    wherein the blend of polyethylene glycol polymers comprises a first polyethylene glycol polymer having a molecular weight within the range of 1350 g/mol to 1650 g/mol and a second polyethylene glycol polymer having a molecular weight within the range of 350 g/mol to 650 g/mol, the bioactive glass comprises from 3% to 7.5% by weight of the composition, the tricalcium phosphate comprises from 15% to 30% by weight of the composition, and the weight percent of the type I collagen or the type I collagen-glycosaminoglycan coprecipitate ranges from 0.2% to 1.5% relative to the total weight of the composition.

2. The composition of claim 1, wherein the tricalcium phosphate and the bioactive glass in the mixture comprise particles dimensioned to fill the bone pores.

3. The composition of claim 1, wherein the collagen component is milled through a screen mesh prior to including in the mixture.

4. The composition of claim 1, wherein all components of the mixture are configured to fill bone pores of a size less than 600 microns.

5. The composition of claim 1, wherein the bone pore filling composition comprises a type I collagen.

6. The composition of claim 1, wherein the bone pore filling composition comprises a type I collagen-glycosaminoglycan coprecipitate.

7. The composition of claim 1, wherein the composition further comprises a hemostatic agent.

8. A method of filling a bone pore or void, comprising administering a composition according to claim 1 to the site of the bone pore or void.

9. The method of claim 8, wherein the composition is applied to the bone pore or void by an individual.

10. The method of claim 8, wherein the composition is injected into the bone pore or void using a syringe.

11. The method of claim 8, wherein the bone pore has a diameter from 75 microns to 350 microns.

12. The method of claim 8, wherein the composition is applied to a bone pore in spongy bone.

13. The method of claim 8, wherein the composition is applied to at least one of a natural bone void or a surgically created void.

14. A bone pore or void filling kit, comprising:
    the bone pore or void filling composition of claim 1;
    a syringe for administering the composition; and
    a sterile package for holding the composition and the syringe.

15. The kit of claim 14, further comprising instructions for filling a bone pore.

* * * * *